United States Patent [19]

Bambara

[11] Patent Number: 5,150,618
[45] Date of Patent: Sep. 29, 1992

[54] ACOUSTIC BEARING DEFECT DETECTOR

[75] Inventor: Joseph E. Bambara, North Babylon, N.Y.

[73] Assignee: Servo Corporation of America, Hicksville, N.Y.

[21] Appl. No.: 622,176

[22] Filed: Dec. 4, 1990

Related U.S. Application Data

[63] Continuation of Ser. No. 376,890, Jul. 6, 1989, abandoned.

[51] Int. Cl.⁵ .................... G01N 29/00; B61K 1/00; G08B 21/00
[52] U.S. Cl. .................... 73/660; 246/169 S; 340/682
[58] Field of Search .................... 73/660, 659, 649; 246/169 S, 169 R, 169 A, 169 D, DIG. 1; 340/429, 682, 683

[56] References Cited

U.S. PATENT DOCUMENTS

| | | | |
|---|---|---|---|
| 3,016,457 | 1/1962 | Brown et al. | 246/169 S |
| 4,129,276 | 12/1978 | Svet | 246/169 S |
| 4,702,104 | 10/1987 | Hallberg | 246/169 R |
| 4,805,854 | 2/1989 | Howell | 246/169 D |

Primary Examiner—Louis Arana
Attorney, Agent, or Firm—Kane, Dalsimer, Sullivan, Kurucz, Levy, Eisele and Richard

[57] ABSTRACT

The present invention relates to bearing defect detectors and in particular to an acoustic system for detecting defects in the bearings of moving railroad cars and identifying the location of these defects.

18 Claims, 4 Drawing Sheets

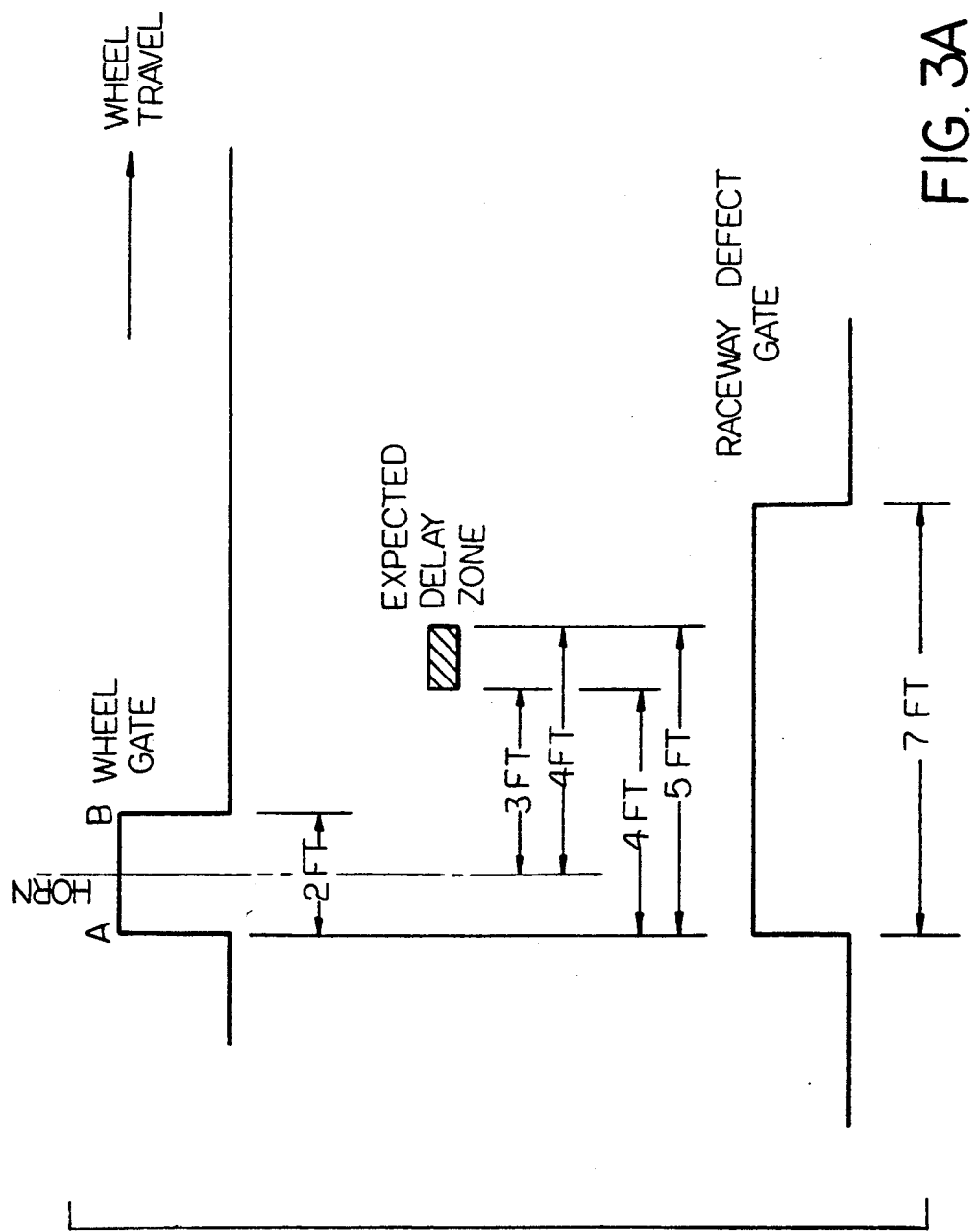

ACOUSTIC BEARING DEFECT DETECTOR

This is a continuation of co-pending application Ser. No. 376,890 filed on Jul. 6, 1989 now abandoned.

BACKGROUND OF INVENTION

1. Field of Invention

The present invention relates to bearing defect detectors and in particular to an acoustic system for detecting defects in the bearings of moving railroad cars.

2. Description of the Prior Art

Heretofore, the detection of defects in railway car bearing has relied upon stationary infrared sensing means along railroad tracks to detect an abnormal heat rise associated with bearing failure in passing railroad cars. While such systems have enjoyed widespread use and an industry-wide reputation for reliability, they suffer from a serious drawback in that they detect a defect only after a damaging heat build-up has occurred within the bearing. Furthermore, this heat build-up often does not occur until a total bearing failure is imminent, thereby normally warranting an immediate stopping of the train so that an emergency field repair may be done. As this requires a delay in the train until a repair team may arrive with the necessary equipment, the total cost of this procedure can be very high.

From U.S. Pat. No. 4,790,190 and pending U.S. patent application Ser. No. 168,975 filed on Mar. 16, 1988, now U.S. Pat. No. 4,843,885, it is known that defects in tapered roller bearings, such as those used in railroad cars, produce sounds, during operation, at characteristic frequencies dependent upon the location or type of defect (i.e., at bearing cup, cone, or roller), the combination of the size of the wheel and the bearing capacity (frequently encountered combinations on railroads are a 28 inch wheel with a 70 ton capacity bearing, a 33 inch wheel with a 70 ton capacity bearing, and a 36 inch wheel with a 100 ton capacity bearing), and the speed of the train (which, of course, for a given diameter of the wheel, is proportional to the rotational frequency of the wheel). Additionally, irregularities in the wheel circumference ("flats") produce a characteristic frequency dependent upon wheel rotational frequency.

Thus, for any given train speed, a defective bearing will produce a sound at one of nine characteristic frequencies dependent upon the location of the defect in the bearing and the combination of the train speed, wheel size and bearing capacity. Wheel flats will produce a sound at one of three additional characteristic frequencies. Ideally, one need only listen for and detect the characteristic sound frequencies to determine the condition of the bearings of the passing train.

Unfortunately, railroad trains operate in extremely noisy environments. Train noises (such as wheel/rail rubbing, flange/rail squeal, loose equipment and cargo sounds, carbody noises, and clacking of rail joints for track circuits) and a wind "swish" are low-frequency sounds which tend to camouflage the impact frequencies produced by a defective bearing. Thus, while the production of characteristic impact frequencies in a moving bearing have been known, it has heretofore been impossible to isolate the impact frequencies in a meaningful manner so as to provide useful and reliable information. More importantly, the background noise may trigger defective bearing alarms and it thus becomes important to be able to distinguish between true defective bearing alarms and alarms set off by this background noise.

OBJECT AND SUMMARY OF INVENTION

It is therefore an object of this invention to provide a means to detect a defective bearing, particularly in on-site railroad applications, before damaging heat build-up has occurred thereby giving repair crews sufficient early warning so as to allow the train to safely run to a place where repairs can be performed conveniently and inexpensively and/or to repair the bearing in its early stages of failure.

It is still another object to determine the location of the defective bearing in the train (car number, axle number and axle side).

It is a further object of this invention to analyze, before repairs begin, the type of bearing defect (i.e., whether the defect is in the bearing cup, cone, or roller) which has occurred.

It is a further object of this invention to detect these defects reliably in a noisy environment such as is common in railroad and other industrial applications.

In analyzing the sounds generated by passing railroad trains, it has been noted that the impact frequencies characteristic of various bearing defects are generated in amplitude-modulated form on an acoustic carrier frequency band which is independent of the speed of the passing train. Thus, while the bearing signature may be a function of train speed, the carrier frequency bands are not.

Therefore, apparatus which includes a microphone is placed beside railroad tracks so as to monitor the sounds emanating from the bearings of a passing railroad train. Preferably, microphones are placed adjacent opposite rails. A series of electronic amplifiers and preliminary filters is used to increase the output of the microphone to a usable voltage level and to filter extraneous frequencies from the resulting electronic signal. This allows the apparatus to operate effectively notwithstanding excessive ambient noise.

The gain of the amplifier is adjusted by the train speed and direction sensor so that the output of the amplifier is relatively constant in spite of significant volume changes due to train speed and direction (in that, under some circumstances, train direction is related to train loads, which is, in turn, related to the volume of noise generated thereby).

After electronic amplification and preliminary filtering, the signal consists predominantly of the preselected carrier frequency band which, in the presence of the characteristic impact frequencies of bearing defects, will be generated within an envelope of the characteristic impact frequencies. In other words, there is an amplitude-modulated signal with a preselected carrier frequency band within an envelope defined by any characteristic impact frequencies which may be present.

Standard amplitude demodulation techniques are used to extract the envelope in which the carrier frequency band is being transmitted. The extracted frequency signal is processed by an array of low-frequency bandpass filters which pass only the frequency ranges in which the various characteristic impact frequencies occur. The center frequencies and the bandwidth of these filters are automatically increased with increasing train speed by the use of switch capacitors, responsive to a train speed and direction sensor.

The array of train speed tuned filters thus performs a spectral analysis of the resulting signal.

The predominant frequency values of the spectrum analyzer are set automatically within its filter frequency range to the expected characteristic impact frequency values of a defective bearing.

When a characteristic impact frequency value falls within the filter range of the filter circuitry of the spectrum analyzer, the operators of the apparatus notify the operators of the train in order that appropriate plans for repair may be made.

BRIEF DESCRIPTION OF THE DRAWINGS

Further objects and advantages of the invention will become apparent from the following description and claims wherein:

FIGS. 3A and 3B show delay gates for a raceway (cup or cone) defect and a roller defect, respectively.

DETAILED DESCRIPTION OF THE PREFERRED EMBODIMENT

Figure 1:
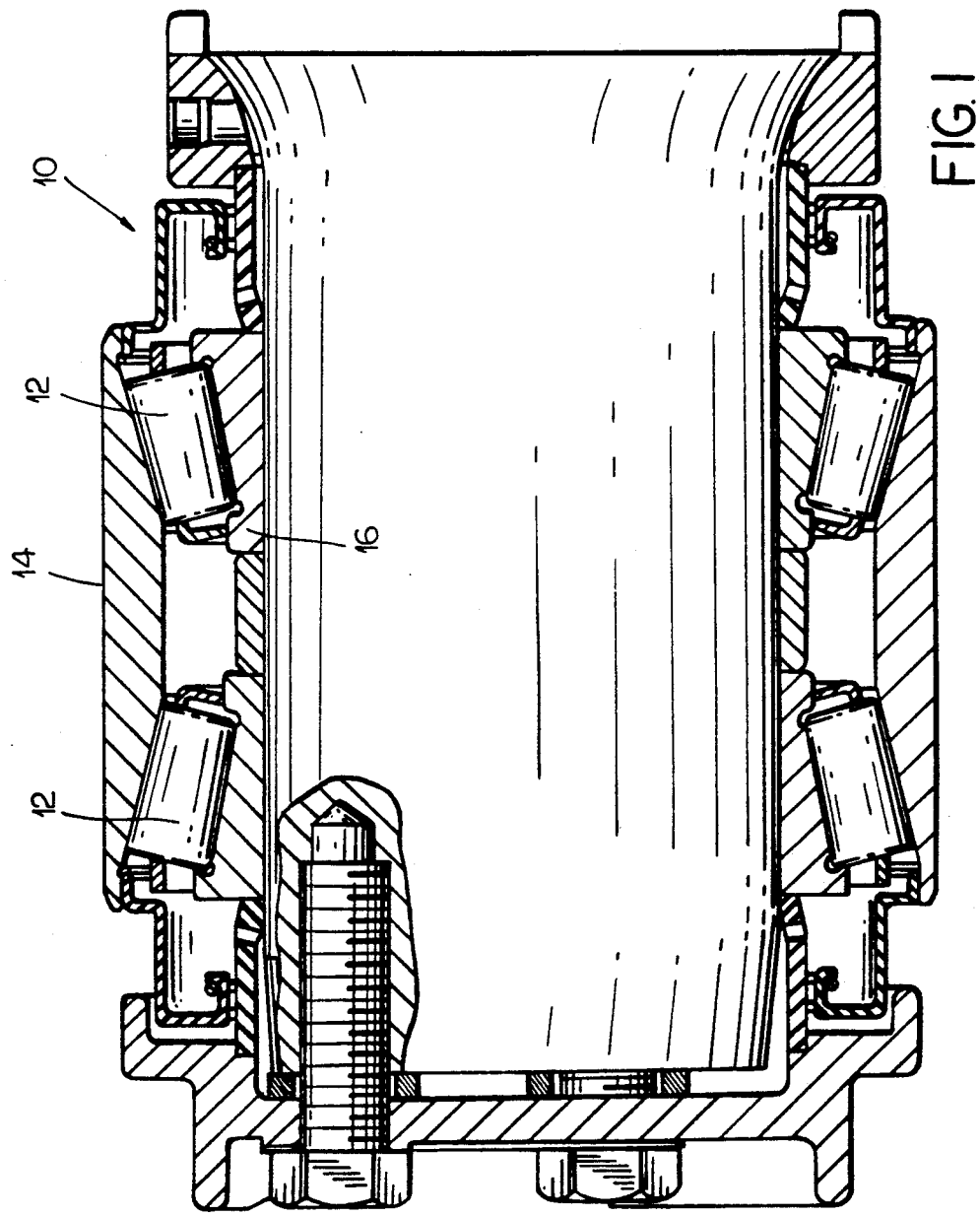
FIG. 1 shows a view in elevation of a typical tapered bearing as is used in railroad applications.

Referring now to the drawings in detail, FIG. 1 shows a tapered roller bearing assembly 10 such as those commonly used in railroad applications. Components which commonly fail because of rolling surface defects (spalls, Brinells, cracks and pits) are the roller 12, the cup 14 and the cone 16. Upon failure of any component, a characteristic component dependent rotational speed-dependent acoustic impact frequency generates a sound spectrum which amplitude modulates a carrier acoustic signal of rotational speed-independent frequency contained within an envelope of said spectrum.

It has been found that the carrier signal has a frequency of approximately 10–12 kilohertz, while sample characteristic impact frequencies for a 6½"×12" bearing assembly (100 ton capacity with a 36" wheel) are listed below:

| Characteristic Impact Frequencies (Hz) | | | |
| --- | --- | --- | --- |
| Defect associated with 36 inch wheel 6½" × 12" bearing assembly (100 ton capacity) | 20 mph | 30 mph | 40 mph |
| roller | 14.6 | 21.9 | 29.2 |
| cup | 32.1 | 48.1 | 64.1 |
| cone | 39.5 | 59.3 | 79.0 |

Figure 2:
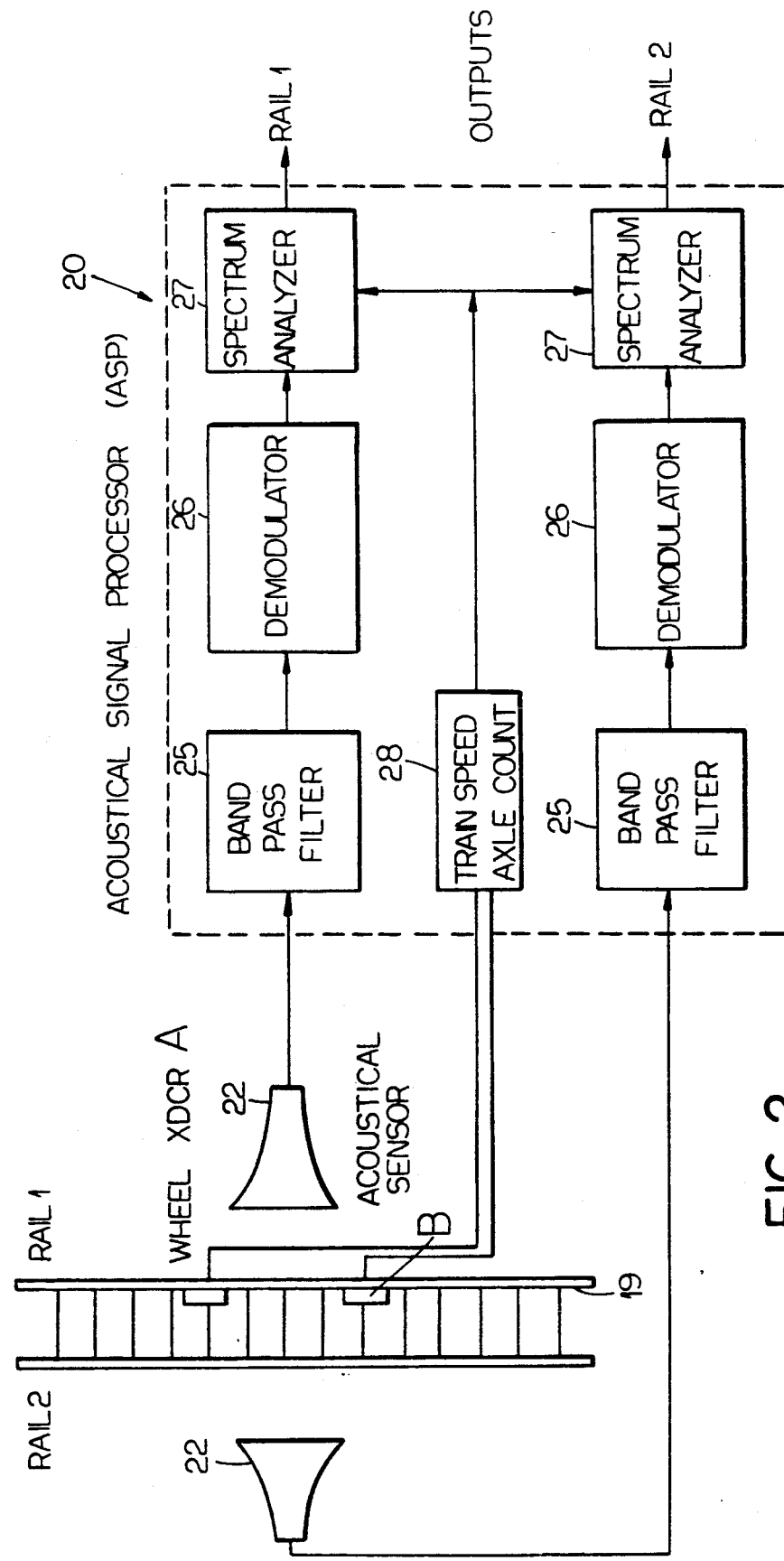
FIG. 2 shows a schematic of the acoustic bearing defect detector apparatus of the present invention.

Referring now to FIG. 2 wherein the acoustical signal processor 20 is shown, input is received from a horn 22 wherein acoustic vibrations are transduced into an electrical signal. Ideally, this is a an electret microphone in a horn assembly with a cavity optimized for the desired bandpass of 10 to 12 kilohertz. A horn is desired as it provides the directional characteristics needed to isolate and identify defective bearing axle locations without ambiguity.

Applicant, after extensive experimentation, has found that placement of the horn assembly is critical so as to avoid picking up excessive background noise (e.g., wheel/rail rubbing; flange/rail squeal; loose equipment or cargo rattling; car-body noise; clacking of rail joints for track circuits). Applicants have found that the horn must not be far back so as to pick up excessive background noise but must be close enough so as to pick up a signature over a horizontal linear distance corresponding to one circumference or rotation of the wheel in order to capture defect repetition rate signatures that generally repeat once per wheel rotation. A wider range than this causes ambiguous results as the horn may monitor different axles simultaneously. A substantially lesser range than this may result in inadequate information for processing. However, a slightly less range than this was found advantageous in order to definitely insolate and locate the axle of interest. Furthermore, the horn should not pick up over a vertical distance above or below the wheel. Therefore, Applicants have found that a horn elongated in the horizontal plane and shortened in the vertical plane to collect acoustic vibrations from a 60 degree horizontal angle and a 20 degree vertical angle (i.e. ±30 degrees horizontally and ±10 degrees vertically from a line perpendicular to the rail) is well adapted to the present purpose. A preferable configuration is to place a horn on both sides of the tracks (one horn for each track). The horn should be placed five feet outboard of the rail gage 19 and collect sounds from a 60° horizontal angle, or somewhat over five feet of track. Additionally, the horn should point horizontally with its horizontal axis 12"–16" above the rail picking up sound vertically from a 20 degree vertical angle for about two feet. Thus, the horn is directed just below the centerline of a wheel.

A horn 22 is placed on both sides of the railroad track so as to monitor the bearings of wheels traversing both rails. Additionally, each horn assembly 22 includes a test tone generator (not shown) which generates a test tone equal to a typical modulation carrier frequency (11.1 kHz) which is modulated sequentially to simulate a range of defects and possible train speeds. The test tone generator on one side of the track is used to generate test tones to calibrate the equipment on the other side of the track during idle periods.

A preamp is incorporated into the horn assembly to amplify the bearing acoustical signature and to prevent the broad range of background noise from overloading later amplifying and processing means. Additionally, a heater and protective shutter are added to the assembly to prevent ambient weather conditions from either damaging or altering the response of the microphone. The shutter opens as the train passes so as to not interfere with the acoustic analysis, but closes thereafter to protect the apparatus from the effects of weather or vandals. Additionally, the heater is turned off as the train passes to prevent the heater from generating alternating current frequency noise.

It will be understood that the circuitry described hereafter is for a single horn 22. Both horns 22 have identical parallel circuitry.

The output of horn 22 is input into the Acoustical Signal Processor 20. The Acoustical Signal Processor 20 extracts the electrical signals related to the resonant metallic sound signatures picked up by the horns 22. The Acoustical Signal Processor 20 includes a bandpass filter 25, a demodulator 26, and a spectrum analyzer 27 for each of the signals output from each of the horns 22 positioned alongside rail 1 and rail 2, as shown in FIG. 2. The spectrum analyzer 27 is implemented by a matrix array of switch capacitor bandpass filters.

Defects on the cup and cone raceways and on the rollers have distinctive characteristic impact repetition rates that are a function of bearing geometry and the rotational rate of an axle, which in turn depends upon wheel diameter and train speed. Chart A illustrates computed impact repetition frequencies for commonly encountered wheel diameter and bearing size combinations for a train speed of 40 m.p.h.

The spectrum analyzer 27 is pre-programmed to recognize the characteristic cup, cone and roller defect frequencies for each of the commonly encountered wheel diameter and bearing size combinations. These frequencies are proportional to train speed and thus the spectrum analyzer 27 is dynamically controlled by train speed information. Two wheel presence transducers A and B, described more fully below, provided information relating to train speed and axle count which is received by circuit 28. Acoustical signatures are correlated with the axle count.

The spectrum analyzer 27 is formed of a matrix of switched

CHART A
DEFECT FREQUENCIES (Hz)

| Train Speed 40 MPH | 36 inch wheel 100 ton bearing | 33 inch wheel 70 ton bearing | 28 inch wheel 70 ton bearing |
|---|---|---|---|
| Cone | 79.0 | 89.5 | 105.5 |
| Cup | 64.1 | 73.5 | 86.6 |
| Roller | 29.2 | 33.8 | 39.9 |
| 1 × Rotation Wheel | 6.22 | 6.79 | 8.00 | capacitor bandpass filters including a 3×3 array of filters for bearing defects on one rail side, a second 3×3 array of filters for bearing defects on the other rail side, and a single 3×1 array for wheel defects on either rail side.

Each filter of the spectrum analyzer 27 is an 8-pole Chebyshev bandpass filter having a nominal ⅓ octave bandwidth (3 dB bandwidth of ±11% of center frequency). The switched capacitor filters have the unique characteristic of a constant normalized filter passband shape with regard to the center frequency.

The center frequency of each filter is determined by an applied clock pulse frequency that is 54.5 times the desired center frequency. For each bearing defect filter its clock pulse frequency is assigned a constant of proportionality with respect to train speed that is dependent on wheel diameter, bearing size and bearing defect type. Similarly, for each wheel defect filter its clock pulse frequency is asigned a constant of proportionality with respect to train speed that is dependent on wheel diameter. Thus, the clock pulse frequencies of the filters in the matrix are controlled dynamically to be proportional to train speed to thereby effectively tune the spectrum analyzer to the expected defect frequencies.

Another feature of the present invention is to provide an exclusive OR network for the output signals of each of the filter arrays of the spectrum analyzer 27. Each exclusive OR network would automatically pass, at any instant of time, the highest output of the associated filter array. For example for one of the 3×3 arrays the associated exclusive OR network would have as inputs all nine outputs of the array and it would exclusive OR gate these outputs so that only the highest output would pass through, while the other eight outputs would be blocked. Thus only the highest output and only the bandwidth of the corresponding filter becomes active as a result of the exclusive OR network to exclude noise in the frequency bands of the remaining filter outputs.

The outputs from each of the three exclusive OR networks can each be applied to an individual track of a multi-track analog chart recorder so that the analog outputs of the 3×3 matrix of bearing defect filters and the 3 X 1 array of wheel defect filters can be displayed and recorded in real time on an analog chart recorder and also converted by means of analog to digital converters, stored in digital memory and printed as an array of numbers representing amplitudes for each bearing and wheel. Outputs exceeding preset levels would trigger alarms. Such levels may be amplitude, area under the curve, etc.

Since wheels with severe flats or other tread defects can generate intense broadband acoustical noise that may stimulate an output from a bearing defect filter, the system can be made to ignore bearing alarms for a specified number of axles ahead of, or after the detection of a flat wheel.

A rather useful real time analog display and recording is obtained by applying the output from the exclusive OR network of one of the 3×3 arrays for one rail side to one track of the analog chart recorder and the exclusive OR network output of the 3×3 array for the other rail side to a second track of the analog chart recorder.

An important feature of the present invention is a window by which a "true" alarm, that is an alarm that is actually triggered by a bearing defect on a specified axle can be distinguished from "false" alarms caused by background noise. If an alarm is within the window then it is associated with the specified axle with the corresponding bearing defect identified by the spectrum analyzer filtering circuit 27, otherwise it is presumed not to be a bearing defect and ignored by the system.

Wheel presence transducers A and B are spaced apart and positioned on the track side to define a gate or window. The two horns 22 are located perpendicular to the rails and midway between transducers A and B. The window defined by transducers A and B corresponds to the detection of a particular wheel/bearing/axle set within the window. The window duration is used to determine train speed. Whether transducer A is followed by transducer B or vice verse determines direction. By counting the number of windows from the head end of the train it is possible to keep track of the number of axles passing through the zone defined by transducers A and B.

As a defective bearing passes the trackside horn 22 corresponding to the side of the train the bearing is on, the output signal of the horn 22 reaches a peak value when the bearing is in the A to B zone due to the horizontal directivity of the horn 22.

Therefore due to the directivity characteristics of the horns 22 and where they are placed, the location of a defective bearing with an abnormally high acoustical signature can be determined in terms of trainside and axle count. The distance between wheel/axle sets can be determined from train speed and the time duration between successive windows. Axle spacing patterns are used to separate axles into those grouped on trucks, and the trucks on cars, so that defect location can then be defined by car count, lead or trail truck on the car, axle position on the truck and axle side.

The propagational delay time of each defect filter in the spectrum analyzer 27 is inversely proportional to the absolute value of its bandwidth which in turn is proportional to its center frequency. The center frequency in the present invention is controlled to be proportional to the train speed. Therefore the propagation delay time of a filter, that is the time delay between when an acoustical signature is received by a trackside acoustical sensor and the time a processed resulting signal is output from the filter, is inversely proportional to train speed.

Since the distance traveled by the train for a given time interval is proportional to train speed, each filter of the spectrum analyzer 27 has a processing delay that is a constant displacement with respect to train movement relative to the location of the horns 22. The propagational delay distance constants of the filters are inversely proportional to their programmed center frequency to train speed proportionality constants. The higher the relative defect frequency the shorter the delay distance.

In the preferred design, the switched capacitor filters have a delay distance of 3 to 4 feet downstream from the location of the trackside horns 22 for the 36 inch wheel/100 ton, 33 inch wheel/70 ton and 28 inch wheel/70 ton cone and cup (raceway) filters.

For the 36 inch wheel/100 ton, 33 inch wheel/70 ton, and 28 inch wheel/70 ton roller filters, the delay distance lies in the range of 7 to 9 feet.

Figure 3B:
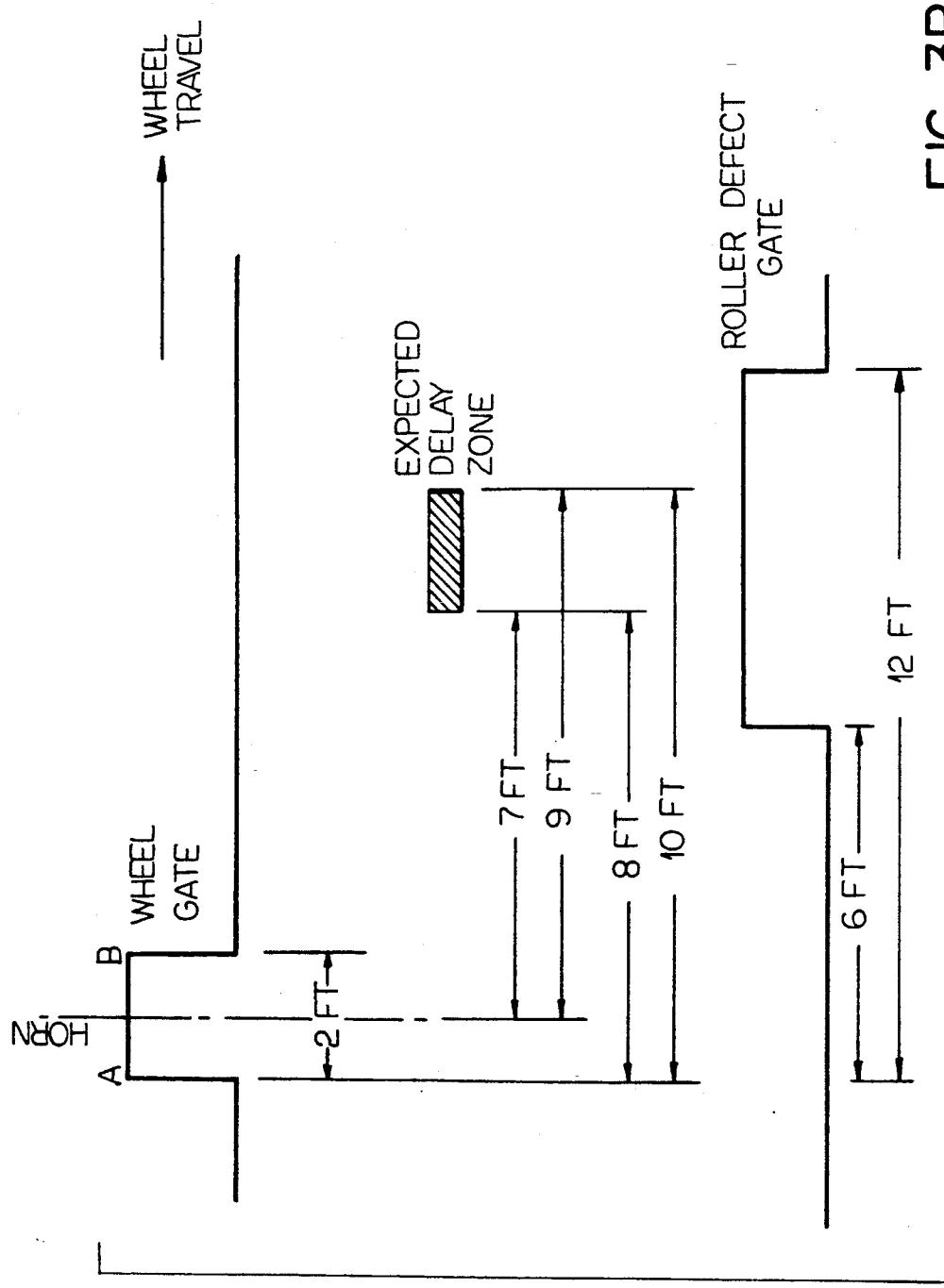

Referring now to FIGS. 3A and 3B, it is preferable to space the wheel presence transducers A and B two feet apart. As shown in FIG. 3A, when a wheel moves from A to B, a raceway defect window is initiated which starts when the wheel is at A and ends either when the wheel is seven feet downstream from A or when a second wheel reaches A, which ever occurs first. For roller defect detection, as shown in FIG. 3B, the window begins when a wheel is six feet downstream of A and ends when the wheel has moved twelve feet downstream of A or when a second wheel passes and moves six feet downstream of A, whichever occurs first. A similar approach is used for train movement from B to A with B as the reference.

Thus false alarms are minimized as are errors in identifying the location of the bearing defect by providing a window for each cone and cup (raceway) defect and also a second window for each roller defect thereby straddling the corresponding propagation delay distances with the associated window. False alarms are those alarms that are not associated with bearings and which may be caused by wheel squeal, wheel defects, and carbody noise.

In the present invention if an alarm exists just prior to the beginning of a window and continues to exist during the duration of that window then it is classified as a false alarm probably caused by background noise. Furthermore, bearing alarms in the vicinity of a wheel defect alarm can be negated. Thus bearing defect alarms eight axles ahead of and four axles after a defective wheel alarm are negated.

Still another feature of the present invention is to have a television camera (not shown) activated by a bearing alarm within a corresponding window where the television camera is aimed at and televises the car and axle having the defect, only when the alarm is generated within the window but not if the alarm is generated before and continues after the window starts.

Obviously numerous modifications may be made to the apparatus without departing from the scope of the invention as defined in the appended claims.

I claim:

1. In an apparatus for acoustically scanning bearings of wheels of a train during operation of said train as said train moves through a scanning zone of a track, said apparatus being of the type including means for transducing acoustic vibrations into electrical signals and means for processing said electrical signals to isolate signals of predetermined impact frequencies indicative of particular bearing defects, the improvement comprising wheel presence transducers on said track for generating signals indicative of the beginning and the end of a window during which an isolated signal is expected to occur for a particular bearing of said train and means to determine if an actual isolated signal associated with said particular bearing occurs within said window.

2. The apparatus according to claim 1 wherein each of said isolated signals is indicative of a particular bearing defect.

3. The apparatus in accordance with claim 1 wherein said wheel presence transducers are positioned within said scanning zone.

4. The apparatus according to claim 1 further comprising means for determining if said isolated signal is at a level for generating an alarm for a particular bearing defect.

5. The apparatus according to claim 1 further comprising horns disposed below a centerline of said wheels to monitor the bearings on said wheels.

6. The apparatus according to claim 1 further including means for generating an alarm signal if said isolated signal occurs within said window.

7. The apparatus according to claim 6, further comprising means for inhibiting said alarm signal if said isolated signal initiates before said window and continues into said window.

8. The apparatus according to claim 6 wherein said means for generating an alarm signal measures the peak value of the isolated signal within the window.

9. The apparatus according to claim 6 wherein said means for generating an alarm signal measures peak value and width characteristics of the isolated signal within the window.

10. The apparatus according to claim 6 wherein said means for generating an alarm signal measures the area of the isolated signal.

11. The apparatus according to claim 6 further comprising means for inhibiting the alarm signal for a specified number of axles prior to and/or after the detection of a flat wheel.

12. The apparatus according to claim 1 wherein said means for processing said electrical signals includes a matrix of switched capacitor bandpass filters set within frequency ranges corresponding to particular bearing defects to identify the bearing defect associated with an alarm generated within said window.

13. The apparatus according to claim 12 wherein said switched capacitor filters have propagational delay times inversely proportional to train speed.

14. The apparatus according to claim 12, wherein said switched capacitor filters includes a first 3×3 array of filters for filtering signals detecting particular bearing defects on one rail side and a second 3×3 array of filters for filtering signals detecting particular bearing defects on the other rail side.

15. The apparatus according to claim 14 wherein said switched capacitor filters further includes a 3×1 array of filters for filtering signals indicative of a wheel defect on either track side.

16. The apparatus according to claim 14 wherein each of said array of filters has outputs and further comprising an exclusive OR network for each of said array of filters, each of said exclusive OR networks passing only the highest output of its associated array of filters while blocking the outputs of the remaining filters.

17. The apparatus according to claim 16 wherein said exclusive OR network bandwidths limits noise to that of the highest input signal.

18. The apparatus according to claim 16 further comprising a multi-track analog chart recorder adapted to receive and display in real time the results from the exclusive OR networks of said first and second 3×3 array of filters and said 3×1 array of filters on first, second and third tracks of said chart recorder, respectively.

* * * * *